United States Patent [19]

Berick

[11] Patent Number: 4,468,124
[45] Date of Patent: Aug. 28, 1984

[54] DOUBLE BEAM PHOTOMETER FOR MEASURING FLUID SAMPLES

[75] Inventor: Alan C. Berick, Albany, Calif.

[73] Assignee: Beckman Instruments, Inc., Fullerton, Calif.

[21] Appl. No.: 493,395

[22] Filed: May 10, 1983

Related U.S. Application Data

[63] Continuation of Ser. No. 235,253, Feb. 17, 1981, abandoned.

[51] Int. Cl.³ .............................................. G01N 21/85
[52] U.S. Cl. .................................... 356/411; 356/435
[58] Field of Search ....................... 356/410, 411, 435

[56] References Cited

U.S. PATENT DOCUMENTS 3,538,337 11/1970 Hrdina ............................ 356/435 X

FOREIGN PATENT DOCUMENTS 2521453 11/1975 Fed. Rep. of Germany ...... 356/435

Primary Examiner—Vincent P. McGraw
Attorney, Agent, or Firm—R. J. Steinmeyer; R. R. Meads

[57] ABSTRACT

A double beam photometric flow cell for high pressure liquid chromatography having illuminated sample and reference passageways therein, the sample passageway receiving flowing fluid sample fractions for analysis. Regulating apertures control the relative amount of light passed through the passageways such that the light energy through the reference passageway exceeds that through the sample passageway. This reduces the contribution of the reference path to "shot noise" in the photometer output signal.

3 Claims, 1 Drawing Figure

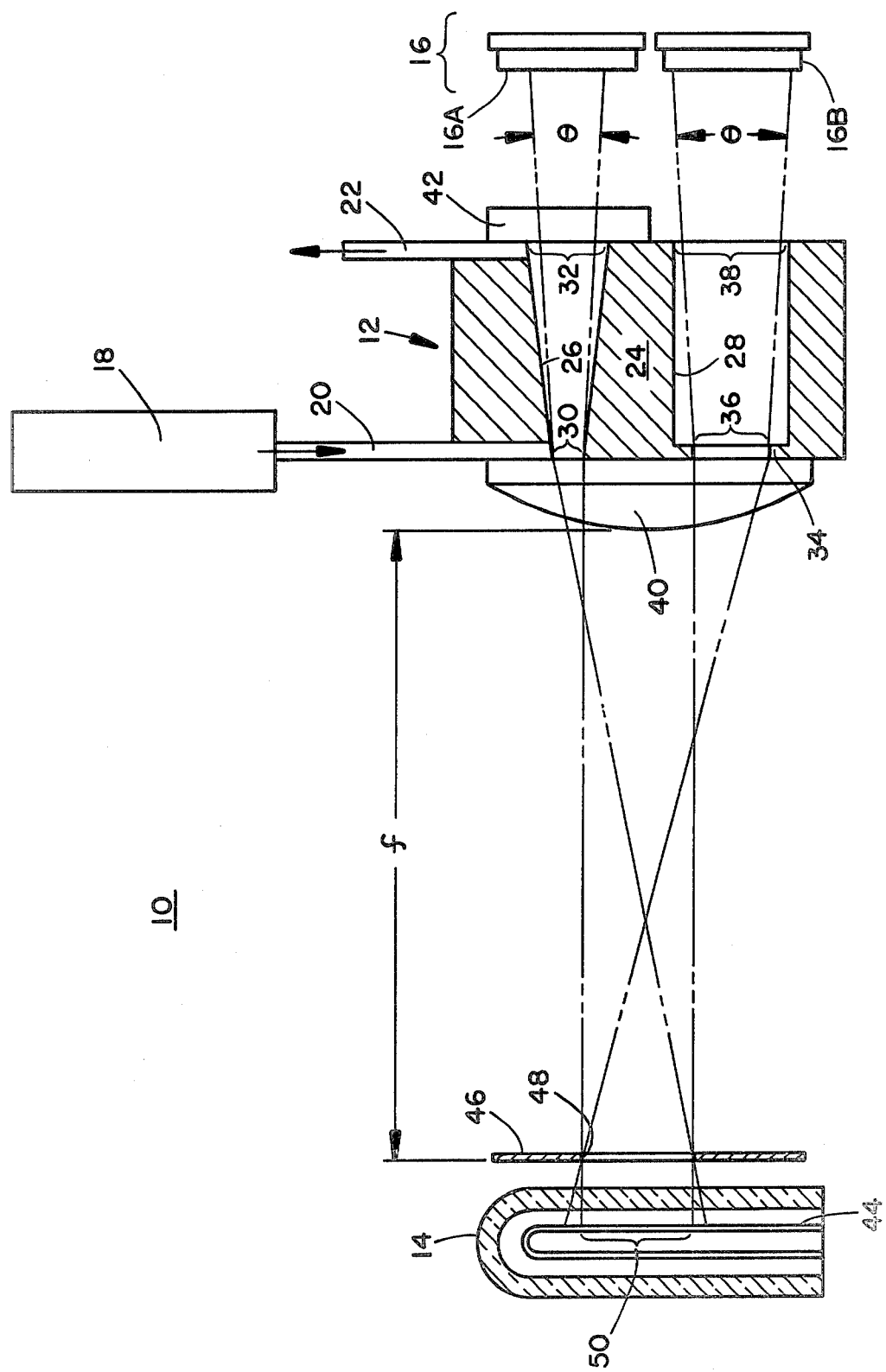

DOUBLE BEAM PHOTOMETER FOR MEASURING FLUID SAMPLES

This is a continuation, of application Ser. No. 235,253, filed Feb. 17, 1981, now abandoned.

BACKGROUND OF THE INVENTION

1. Field of the Invention

The present invention relates generally to measurement of fluid samples and, more particularly, to optical measurement of such samples in a photometric flow cell. The invention is particularly suited for use in a liquid chromatographic system where a stream of successive fluid sample fractions eluted from a chromatrographic column is flowed through a photometric flow cell for analysis of individual sample fractions.

2. Description of the Prior Art

Double beam photometers have long been used in fluid flow systems to optically measure fluid samples. In one common form, such photometers comprise a flow cell body having a pair of light transmissive passageways—a sample passageway configured to receive a fluid sample and a reference passageway configured to receive a reference fluid or no fluid at all. Light from a source is split into a sample beam and a reference beam and passed through the corresponding sample and reference passageways and hence through any sample or reference fluid therein. A light detector intercepts light emerging from the respective passageways to derive a ratio measurement of sample and reference beam energy and hence a measure of a characteristic (usually absorbance) of the sample. A principal advantage of a double beam system is its inherent ability to reject common mode noise effects in the two paths, and hence to generate an output signal exhibiting a high common mode rejection ratio.

In this pressure liquid chromatography (HPLC), double beam flow cell photometers have been adapted to receive and optically measure a stream of successive fluid sample fractions eluted from a chromatographic column. The sample fractions (carried in a solvent matrix) are typically minute in volume (e.g. 100 $\mu$l–1.0 ml), closely spaced, low in concentration, and are flowed at high pressure up to as high as about 40 atmospheres in the flow cell.

In designing double beam flow cells for HPLC applications, configurations are desired which measure sample fractions with maximum resolution and sensitivity. Resolution is an indication of the system's ability to distinguish measurements of successive, closely spaced flowing samples, i.e. to distinguish the "peaks" generated in the photometer output optical signal representative of such samples. Sensitivity is an indication of the minimum concentration or amount of sample which must be present to be distinguished as sample from the baseline noise of the photometer output signal. In these respects a common prior flow cell configuration comprises sample and reference passageways identical in size and shape. Apparently, identical sample and reference passageways were felt to be desirable to provide a symmetry or balance in the optics geometry of the flow cell to establish adequate common mode rejection and resolution for the system.

As prior flow cell designs have been perfected, so-called "shot"noise in the photometer output signal has become a more significant factor. Shot noise is a high and low frequency noise signal superimposed on the output optical baseline signal of the photometer which is believed to represent statistical variations in light beam intensity. The effect of the shot noise signal is to decrease the sensitivity of the photometer. By decreasing system sensitivity, shot noise impairs the system's ability to measure samples of low concentrations. In effect, then, the performance of the prior flow cells, though improved, has become limited by shot noise. One possible approach for contending with shot noise is to increase the light energy level in the sample passageway by increasing the passageway diameter. While such effects a shot noise reduction, it is at the expense of a substantial decrease in system resolution.

Accordingly, a need exists for a double beam photometer for receiving and measuring fluid samples without the drawbacks of the prior art. The present invention meets these needs.

SUMMARY OF THE INVENTION

The present invention resides in an improved double beam photometer for measuring fluid samples in a manner which overcomes the drawbacks of the prior art. The improved photometer exhibits high sensitivity together with high resolution and high common mode rejection. The improved double beam arrangement is achieved in a commercially practical form which is simple and inexpensive in construction and reliable in operation.

To the foregoing ends, the present invention is embodied in a photometer of the type comprising: (1) a light source, (2) means defining first and second light transmissive paths configured to receive light from the source and to pass the light therealong and through a fluid sample in at least one of the paths, and (3) means for measuring the relative intensity of the first and second beams upon emergence from the beam paths to derive a measure of the sample. Applicant has discovered that increasing the relative energy of light in the reference beam path to exceed that of the sample beam path reduces shot noise in the photometer output signal, thereby increasing system sensitivity, while maintaining the desired optical resolution and common mode rejection ratio of the photometer. In a preferred embodiment, the improved design is achieved by regulating means comprising limiting apertures for light entering each optical path with the limiting aperture for the reference beam path being larger than that for the sample beam path.

In the preferred embodiment, the sample and reference beam paths are through corresponding sample and reference passageways of a flow cell body. The regulating means comprises limiting apertures for light entering each passageway, the limiting aperture for the reference passageway being larger than that for the sample passageway.

The invention further contemplates means cooperating with the light source to define a given area of the source from which light is passed to the sample and reference beam paths. Such an arrangement reduces parallax problems which can occur when the areas of the source viewed by sample and reference are not coincident and which in turn lead to poor common mode rejection if the source has spatial variations in intensity.

BRIEF DESCRIPTION OF THE DRAWING

The FIGURE is an optical diagram of a double beam photometer of the present invention as incorporated in an HPLC system and illustrates in vertical cross section the flow cell of the photometer. Limiting rays of optical beam paths of the photometer are illustrated in phantom outline.

DESCRIPTION OF THE PREFERRED EMBODIMENT

As shown in the drawing, the present invention is embodied in a double beam photometer 10 comprising a double beam flow cell 12 disposed in an optical path between a light source 14 and an optical detector 16. The flow cell is adapted to receive liquid sample fractions flowed under pressure from a liquid chromatograph colum 18 through a supply conduit 20 and to discharge the sample after analysis through a discharge conduit 22. The discharge conduit is connected to a back pressure regulator (not shown) for establishing a requisite pressure in the flow path from column 18 through the flow cell 12. Typically, the discharge conduit is connected to a suitable waste receptacle or sump into which the fluid is flowed.

The flow cell 12 comprises a generally cylindrical body 24. A pair of generally parallel sample and reference passageways 26 and 28, respectively, extend between the ends of the body 24. Supply conduit 20 opens into one end of sample passageway 26 while discharge conduit 22 opens into the opposite end of the same passageway. With such an arrangement, sample fractions eluted from column 18 are flowed under pressure through supply conduit 20 into sample passageway 26, through the sample passageway, and out discharge conduit 22 to waste. Reference passageway 28 may include similar supply and discharge conduits (not shown) at its opposite ends for flowing reference fluid into and out of the reference passageway. In flow cell 12, however, such conduits are omitted since the flow cell is primarily employed for sample analysis without the presence of a reference fluid in the reference passageway.

The walls of sample passageway 26 are tapered conically outwardly in the direction of fluid flow from supply conduit 20 to discharge conduit 22. The walls thus define a opening or aperture 30 at the frustum of the conical passageway and a relatively larger opening or aperture 32 at the base of the cone.

The reference passageway 28 is of generally cylindrical configuration. Body 24 forms an annulus 34 at the left end of the passageway which defines an opening or aperture 36 at such end. A relatively larger opening or aperture 38 is defined by the cylindrical wall at the opposite end of the reference passageway.

The left end openings 30 and 36 of the respective sample and reference passageways are closed by a light transmissive window 40 sealed to the end of the flow cell body 24. Window 40 is also configured as a collimating lens for light entering the sample and reference passageways. The opposite end of the sample passageway 26 is closed by a second light transmissive window 42. A clamp (not shown) retains windows 40 and 42 in place on the flow cell body 24 in a fluid-tight seal against the body. In the preferred embodiment of flow cell 12, the opposite or right hand end of the reference passageway 28 is open leaving the reference passageway exposed to the atmosphere. However, in the event the reference passageway were adapted to receive a reference fluid, then a further window or an extension of window 42 would be provided sealed to the right face of body 24 for closing this end of the reference passageway.

Light source 14 is a gas discharge lamp having a generally U-shaped zone 44 of light emission at a selected wavelength. A mask 46 having an aperture 48 is positioned adjacent the lamp to define a given area 50 of the source emitting zone 44 from which light is passed by aperture 48 toward the flow cell 12. The light passed by aperture 48 is received and collimated by lens/window 40 and passed thereby as first and second light beams along paths through respective sample and reference passageways 26 and 28. Light emerging from the flow cell passageways 26 and 28 impinges on detectors 16a and 16b, respectively, which, in turn, generate output current signals idicative of the light energy striking each detector.

Optical analysis of the flowing sample fractions is performed in a conventional manner by measuring an optical characteristic of each sample fraction (e.g. absorbance) at the selected wavelength as the sample flows through passageway 26. In this regard, the output current signals of detectors 16a and 16b, representative of the energy of the sample and reference beams, respectively, exiting passageways 26 and 28, are processed to compare (as by ratioing) the sample and reference beam energies to derive a measure of the sample alone.

It will be noted that the sample and reference passageways 26 and 28 are configured so as to pass the respective sample and reference light beams therethrough without the light striking the interior walls of the passageways. Such minimizes noise caused by light deflecting from the passageway walls toward the detectors. The conically tapered wall of the sample passageway 26 contributes to such a result. Thus, even if a stream of sample fractions exhibiting changes in refractive index is flowed through passageway 26, such refractive index variations do not cause spurious deflection of radiation from the passage walls or corresponding output signal noise. In reference passageway 28, the entrance aperture 36 and the comparatively larger exit aperture 38 cooperate to accommodate passage of a generally conical beam through the passageway without the beam striking the passageway walls.

As previously mentioned, a primary aspect or feature of the present invention is the significant reduction in shot noise superimposed on the optical baseline output signal of the photometer. In that regard, it has been discovered that such significant reduction is achieved by regulating the relative light energy admitted through the reference and sample passageways such that the light energy in the reference beam exceeds that of the sample beam. Moreover, such noise reduction is achieved while minimizing noise due to refractive index variations and while maintaining high optical resolution and a high common mode rejection ratio.

To the foregoing ends and in accordance with the invention, the relative diameters of entrance apertures 36 and 30, respectively, to the reference and sample passageways 28 and 26 are controlled such that aperture 36 is larger in diameter than aperture 30. The apertures thus serve as means for regulating the relative energy of light in the beam paths such that more light energy is admitted into the reference passageway 28 and passed to corresponding reference detector 16b compared to the light energy reaching detector 16a through the sample passageway 26. In the preferred embodiment the diameter of reference passageway aperture 36 is approximately 1.4 times greater than the diameter of sample passageway aperture 30.

The significance of the increase in reference beam light energy with respect to the sample beam energy is illustrated as follows. Statistical fluctuations in the output current of a photodetector such as 16a or 16b is represented by $$\frac{\Delta I}{I_0} = \sqrt{\frac{k}{I_0}}$$

where $I_0$ equals the average d.c. outut current of the photodetector and k equals a constant independent of $I_0$. When the output signal of the overall detector 16 is the ratio of the output currents of the sample and reference beams, the total fluctuation in output signal of detector 16 is represented by:

$$\frac{\Delta R}{R} = \sqrt{k} \sqrt{\frac{1}{I_s} + \frac{1}{I_r}}$$

where $I_s$ equals the output current of sample beam detector 16a, $I_r$ equals the output current of the reference beam detector 16b, and R equals the ratio of the output currents. Since the magnitude of these statistical fluctuations in the detector output is inversely proportional to the square root of the output current, it appears advantageous to maximize the light energy in both sample and reference beams. However, the light energy of the sample beam is limited by the sample passageway volume, which is limited by the volume of the sample measured, which is in turn limited by the resolution requirement of the photometer. Significantly, however, applicant has recognized that no such limitation of light energy is required for the reference beam.

With respect to the foregoing, assume, for example, that $I_r$ equals $I_2$. In such case it can be shown by the foregoing equations that the total output shot noise is about 41% greater than that for the sample beam alone. However, if $I_r$ is twice that of $I_s$, then the total output shot noise is only 22% greater than that of the sample beam alone. Moreover, if $I_r$ is four times greater than $I_s$, then the total shot noise is only 12% greater than that for the sample beam alone, and so on. Therefore, the result of increasing light energy in the reference beam relative to that in the sample beam is to correspondingly decrease the optical baseline shot noise in the detector output signal without sacrificing the superior common mode rejection ratio or high sensitivity of the double beam system. In effect, increasing the energy in the reference beam relative to that of the sample beam substantially reduces the contribution of the reference beam to the output shot noise level.

In dimensioning the photometer 10 in accordance with the invention, aperture 48 is placed as close to light source 14 as feasible to define the given source area 50 for viewing by both sample and reference passageways. This reduces parallax problems which can occur when the areas of the source viewed by the sample and reference passageways are not coincident and which, in turn, lead to poor common mode rejection if the source has spatial variations in intensity. The beam dispersion angle $\theta$ is selected so as to minimize the interior volume of flow cell sample passageway 26 to ensure adequate sample resolution while assuring an adequate light throughput for minimum optical baseline noise. In this regard $\theta$ is defined as $$\frac{2\tan^{-1}d}{2f},$$

where f is the focal length of lens 40 at the wavelength of use (here 254 nm) and d is the diameter of aperture 48. Once $\theta$ is fixed, the size of aperture 48 is adjusted to view as large an emitting zone 50 of the source 14 as feasible which completely fills the aperture with light. When this maximum dimension of aperture 48 is attained, then f will be a maximum fixed by the maximum aperture dimension and by $\theta$. Maximizing f tends to minimize the parallax problem.

While the nature and type of optical components in the foregoing system will vary depending upon the application and type of samples to be measured, one successfully operated system incorporated in a liquid chromatograph was constructed in accordance with the following specifications. Source 14 is a mercury lamp which emits at 254 nm. Aperture 48 of mask 46 is 0.125 inch in diameter. Lens 40 has a focal length of 2.0 inches, an operating focal length at 254 nm of f=1.787 inches and is spaced from mask 46 by this distance f. Entrance opening 30 of sample passageway 26 is 0.05 inches in diameter while, in accordance with the present invention, entrance opening 36 of the reference passageway is 0.07 inches in diameter. Both passageways have a path length through body 24 of 10 mm. $\theta$ or the beam dispersion in flow cell 12 is 3.96°. Detector 16a and 16b have 5 mm diameter light sensitive areas spaced 7 mm center-to-center. The distance from the rear or right end of flow cell 12 to the detectors is 10 mm.

While photometer 10 has been illustrated with sample passageway 26 conically tapered and reference passageway 28 cylindrical, it will be understood that both could be conical or both could be cylindrical. Preferably conical beam paths through the passageways 26 and 28 are defined by the entrance and exit openings thereof. In another form, the passageways 26 and 28, instead of being generally parallel, are disposed at an angle such that their axes when extended rearwardly toward source 14 meet or converge so as to view a limited or focal area of the source.. In this form, the collimating function of lens/window 40 is unnecessary.

While a preferred embodiment of the invention has been illustrated and described, it will be apparent that modifications may be made therein without departing from the invention defined in the appended claims.

What is claimed is:

1. A method of operating a double beam flow cell photometer of the type comprising a light source, means defining sample and reference light beam paths configured to receive light from the source and pass the light therealong and through a fluid sample in the sample beam path, means for flowing fluid samples into and from the path of the sample beam, said method including the steps of:

positioning first and second detectors proximate one another in the respective sample and reference beam paths and subject to the same environment for measuring the relative intensity of the sample and reference beams upon emergence from the beam paths;

directing light from the source along the beam paths toward the first and second detectors to derive an output signal providing a measure of the effect of the fluid sample on the sample light beam, the output signal including a shot noise signal component;

generating respective sample and reference beam output current signals $I_s$ and $I_r$ such that for the ratio R of the output current signals $I_s$ and $I_r$ the total fluctuation of the ratioed output signal $\Delta R/R$ is proportional to $$\sqrt{\frac{1}{I_s}+\frac{1}{I_r}};$$

and regulating the relative energy of light in the beam paths such that the energy in the reference beam path exceeds that in the sample beam path whereby the output current signal $I_r$ exceeds output current signal $I_s$ so that the contribution of the reference beam to the output shot noise level is reduced.

2. In a double beam flow cell photometer for measuring a fluid sample of the type comprising a light source, means defining sample and reference light beam paths configures to receive light from the source and pass the light therealong and through a fluid sample in the sample beam path, means for flowing fluid samples into and from the path of the sample beam, the improvement comprising:

detector means including first and second detectors situated proximate one another in the respective sample and reference beam paths and subject to the same environment for measuring the relative intensity of the sample and reference beams upon emergence from the beam paths to derive a detector output signal providing a measure of the effect of the fluid sample on the sample light beam, which output signal includes a shot noise signal component, said first and second detectors being responsive to the respective light beam energies to generate respective sample and reference output current signals $I_s$ and $I_r$ such that for the ratio R of the output current signals $I_s$ and $I_r$ the total fluctuation of the ratioed output signal $\Delta R/R$ is proportional to $$\sqrt{\frac{1}{I_s}+\frac{1}{I_r}};$$

and means for regulating the relative energy of light in the beam paths including limiting apertures for light in each of the beam paths, the limiting aperture in the reference beam path being larger than that in the sample beam path such that output current signal $I_r$ exceeds output current signal $I_s$ whereby the detector means and regulating means cooperate to reduce the contribution of the reference beam to the shot noise level in the output signal of the detector means.

3. The photometer of claim 2 wherein the limiting aperture in the reference beam path has a diameter 1.4 times greater than that of the limiting aperture in the sample beam path.

* * * * *